United States
Baumoel

4,144,517
Mar. 13, 1979

[54] SINGLE TRANSDUCER LIQUID LEVEL DETECTOR

[76] Inventor: Joseph Baumoel, 107 Columbia Dr., Jericho, Long Island, N.Y. 11753

[21] Appl. No.: 822,199

[22] Filed: Aug. 5, 1977

[51] Int. Cl.² ............................................. G01F 23/28
[52] U.S. Cl. .................................. 340/1 L; 73/290 V; 73/599
[58] Field of Search .......................... 340/1 L, 244 R; 73/290 V, 599, 600

[56] References Cited

U.S. PATENT DOCUMENTS

| 3,407,398 | 10/1968 | Stearn | 340/244 R |
| 3,427,867 | 2/1969 | Nute et al. | 73/599 |
| 3,553,636 | 1/1971 | Baird | 340/244 R |
| 3,603,149 | 9/1971 | McKown | 73/290 |

FOREIGN PATENT DOCUMENTS

720970  11/1965  Canada ................. 340/244 R

*Primary Examiner*—Richard A. Farley

*Attorney, Agent, or Firm*—Ostrolenk, Faber, Gerb & Soffen

[57] ABSTRACT

The presence or absence of liquid at a particular location of a tank or pipe is sensed through the wall of the container by a single ultrasonic transducer which may be secured to the outer surface of the container by hand pressure, by clamping, or by cementing. Detection is obtained through the damping effect of either liquid or air within the container on multiple interface reflections of a longitudinal sonic beam in the container wall. The first return signal amplitude adjusts the gain of the monitoring circuit and allows the measurement of the percentage decay of the return signal and the comparison of the decay to the known decay rate if the container was either empty or full at the point of measurement. Output circuits are provided to give a full or empty output signal, or to provide output control signals in response to the fluid level measurement. A fault alarm signal is also produced to indicate that the transducer is not properly coupled to the container or that the circuit is working improperly.

20 Claims, 8 Drawing Figures

ULTRASONIC TRANSMIT PULSE AMPLITUDE $V_{Tx}$ → TIME $V_{SIG}$ AMPLITUDE OF RETURN SIGNAL FOR LIQUID FILLED CONTAINER $V_{REF}$ $T = \frac{2w}{v_S}$

→ TIME $V_{SIG}$ AMPLITUDE OF RETURN SIGNAL FOR EMPTY CONTAINER $V_{REF}$

→ TIME

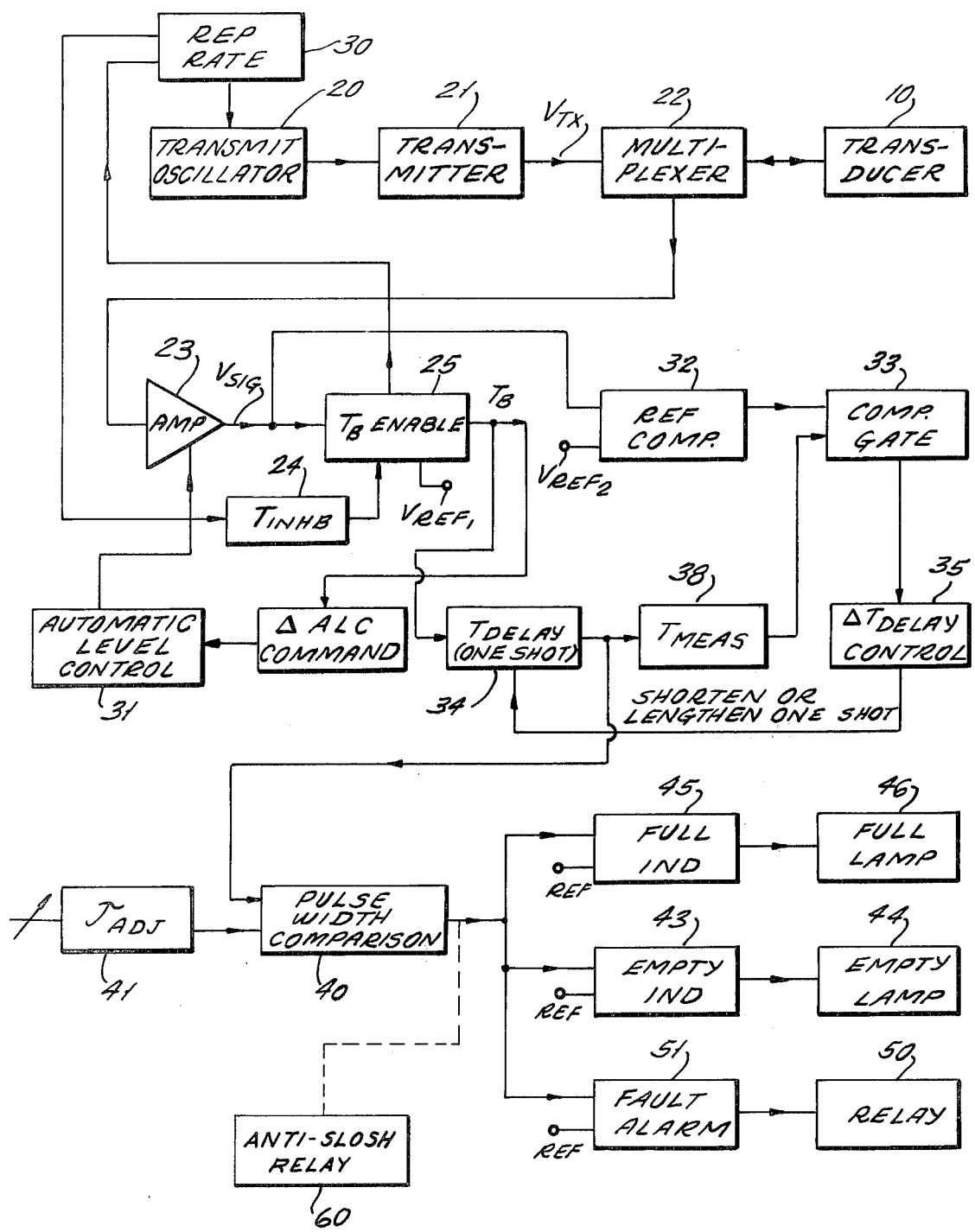

SINGLE TRANSDUCER LIQUID LEVEL DETECTOR

BACKGROUND OF THE INVENTION

This invention relates to a novel liquid level detector for detecting the presence or absence of a liquid in a container, and more specifically relates to a novel ultrasonic circuit which includes an ultrasonic transducer which can be pressed against the outer wall of a liquid container such as a tank or pipe and which will produce an output signal which indicates whether there is a liquid in the container at the transducer location.

It is frequently desirable to determine whether a pipe or container is filled with a liquid or to determine the height of a liquid within a container. This is commonly done by gauges or other equipment which must penetrate the container wall and reach into the interior of the pipe or container. These gauges are then used to produce an indication of liquid level or the presence of liquid in the container, and can be used to operate liquid flow or liquid level controls. The need to gain access to the container interior has the obvious drawbacks of requiring special container designs and, in some cases, special seals to bring out gauge components, electrical wires, and the like. Moreover, these parts become subject to failure when exposed to corrosive fluids and hostile environments within a liquid container.

BRIEF DESCRIPTION OF THE INVENTION

The present invention provides a novel ultrasonic measuring system which includes a transducer which can simply be pressed against the outer wall of a container or pipe and will give an output signal indicating the presence or absence of liquid in the container adjacent the transducer location. Thus, the liquid presence measurement can be made without having to penetrate the container wall and the output signal can be used, as desired, to indicate the presence or absence of liquid at the transducer level, or to control liquid flow or level in the container. The novel system of the invention is also operable to identify the liquid within the container, depending on the sonic characteristics of the liquid.

The transducer system is small enough to be portable or, if desired, it can be clamped or cemented in place on a given container. The system is operable for pipe walls of various materials including metal and plastic of almost any thickness. Fault sensing means are also provided to produce signals indicating that the transducer is not coupled to the container, or that the measurement circuit is not functioning properly.

The novel control circuit of the invention makes the output signal independent of the pressure with which the measuring transducer is pressed against the wall. Thus, the system can conveniently be used by personnel with little training.

In one embodiment of the invention, the transducer is spring-loaded against the container, thus eliminating the need for any judgment by the user.

The principle of operation of the system is to apply a longitudinal ultrasonic energy pulse into the pipe or container wall. The ultrasonic pulse will undergo multiple internal reflections in the pipe wall, and the amplitude of the multiple reflections will decrease, or decay, at a rate dependent upon the sonic impedance of medium within the container and at the interface with the interior surface of the container wall. If the pipe is empty at the point where the measurement is made, the rate of decay of the interface reflections will be lower than if the pipe is filled with liquid at that point. Thus, a measure of the rate of decay of the amplitude of the multiple internally reflected signal will determine whether or not there is fluid behind the container wall portion which receives the transducer probe.

Since the sonic impedance of various liquids differs, the accurate measurement rate of decay will also allow the identification of the liquid in the container.

In making the rate of decay measurement, the transducer is first calibrated by placing it against a portion of the container which is known to be empty. Note that calibration could also be obtained by placing the transducer at a location known to be filled. The time required for the multiple wall reflections to decay from a given reference level to some reduced value, such as twenty percent of the given reference level, is then measured and is later used as a reference delay time. The transducer is then used to make a measurement at some point on the container and the time taken for the return signal to decay from the first reference level to the twenty percent level is measured. If this time is much shorter than the reference decay time, then there is liquid at that point. If the decay time is about the same as the reference decay time, then the container is empty at that point. The transducer may then be moved along the container in order to locate a liquid level, or the transducer may be fixed in place to provide a full or empty output signal to indicating, and/or, control equipment.

To avoid the need to couple the transducer to the container with a constant pressure and to eliminate the need for exactly reproducable coupling, a novel circuit is provided whereby the first reference level is set by the first return pulse sensed by the transducer after the noise of the initial energy pulse into the tube wall has ceased. Thereafter, the circuit measures amplitude decrease from this constant reference point, and this measurement is independent of the coupling between the transducer and the pipe wall.

If the transducer is not properly coupled to the container, the first return signal will not be high enough to create the first reference signal level even at full amplifier gain. Under this condition, an alarm will be sounded. Similarly, if the first reference signal or the second lower reference signal is produced within the measuring interval, and is therefore produced for some spurious reason, such as amplified noise or the like, an alarm will be sounded.

The circuit is also equipped with an adjustable anti-slosh time delay circuit to prevent an alarm signal due to sloshing of liquid in the tank or container.

BRIEF DESCRIPTION OF THE DRAWINGS

FIG. 3 is a functional block diagram of the novel circuit of the present invention.

DETAILED DESCRIPTION OF THE DRAWINGS

Figure 1:
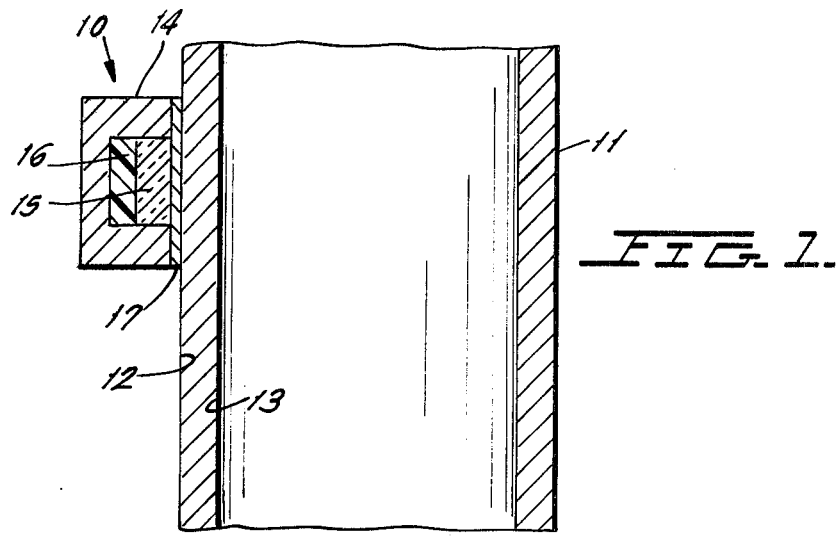
FIG. 1 is a schematic cross-sectional view showing a single transducer pressed against the wall of a container.

FIG. 1 schematically illustrates a transducer 10 fixed to the outer wall of a container 11. Container 11 can be any type of fluid container and can be a pipe, a barrel, or the like, which has any fluid stored or flowing therein.

Container 11 is shown as a pipe in FIG. 1 and the pipe may be circular in cross-section, although the container 11 can have any configuration. The wall of container 11 may be of any of a variety of materials which conduct ultrasonic energy, and which exhibit multiple reflections of ultrasonic energy introduced from the outer surface of the pipe and between inner wall surface boundaries 12 and 13 of the container wall. Materials for container 11 may typically be steel, brass and a variety of plastics, and the wall thicknesses may be any desired thickness which typically could range from 1/64 inch to 3 inches.

Transducer 10 may be of any desirable design and is used to introduce a longitudinal ultrasonic pulse into the wall of container 11 which pulse is directed perpendicularly to the wall, and which will undergo multiple internal reflections at wall surfaces 12 and 13. Transducer 10 is also operable to produce an output signal which is related to the amplitude of the reflected ultrasonic pulse which it receives from the surface 13.

Transducer 10 may have a steel housing 14 which receives a lead metaniobate crystal 15 which is backed by a sound-absorbent layer 16 which may be of tungsten loaded epoxy. Leads, not shown, are connected to crystal 15 and a suitable voltage connected to these leads causes crystal 15 to produce a sharp sonic wave into the wall of container 11, and permit the production of an output voltage in response to the reflected ultrasonic waves. The use of lead metaniobate is preferred since it prevents ringing and produces a sharp output pulse at a frequency, for example, of 10 megahertz.

Transducer 10 can be secured to container 11 in any desired manner. Thus, it may be secured by cementing with an epoxy cement which insures good sonic connection between the container 11 and transducer 10, or it can be clamped to the container 11 by any suitable clamping structure (not shown). One suitable clamping structure is that shown in U.S. Pat. 3,987,674, in the name of Baumoel, entitled "*TRANSDUCER STRUCTURE AND SUPPORT FOR FLUID MEASURING DEVICE*".

When clamping is used, a coupling medium layer 17 such as glycerine or silicone oil or the like should be used between the transducer 10 and container 11. When small diameter pipes are used, a flat should be placed on the pipe where it receives transducer 10 to insure coupling between the pipe and transducer. Note that the transducer 10 may also be shaped to conform to the container wall surface.

Transducer 10 may also be a fully portable element, and can be simply pressed against any part of the surface of container 11 to determine whether there is liquid at the level of the transducer 10.

One or several permanent or semi-permanent transducers may be mounted at different locations or heights of a container, and can be connected for any desired control scheme.

When transducer 10 is pulsed, it produces a sharp, longitudinal ultrasonic wave which propagates into the wall of container 11 and toward surface 13. The amplitude of the first return signal reflected from surface 13 is a function of the voltage applied to the transducer, the degree of coupling of the transducer to container 11, the sonic impedance of wall of container 11, and the sonic impedance of the medium within container 11 at the transducer location. The medium will be a liquid if the container is filled at the transducer location or air, for example, if the container is empty at the transducer location.

The reflected pulse reaches interface 12 in a time $T = (2\omega/v_3)$, where $\omega$ is the wall thickness and $v_s$ is the velocity of sound in the container wall, and the pulse return is sensed by transducer 10 and is re-reflected toward interface 13. The magnitude of the pulse next reflected by interface 13 will be attenuated, relative to the first reflection therefrom, by an amount which is a function of the sonic impedances of the container wall and of the medium within the container, and by the attenuation in the container wall itself. Thus, the amplitude of each subsequent return signal will decay at the rate dependent on the sonic impedance in the medium within container 11 which is relatively high if the medium is liquid and relatively low if the medium is a gas. Consequently, the multiple internal reflections in the container wall will be rapidly attenuated if the container contains a liquid at the measurement location, and will be less rapidly attenuated if the container is empty at the measurement location. Moreover, the attenuation will be different for different liquids, this allowing the device to discriminate between different liquids.

Figure 2A:
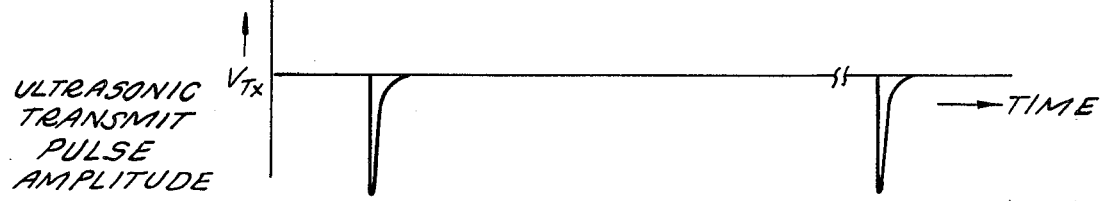
FIGS. 2a, 2b and 2c are plotted on a common time scale and respectively illustrate the input ultrasonic pulse amplitude, the return signal for a liquid-filled container, and the return signal for an ampty container.
Figure 2B:
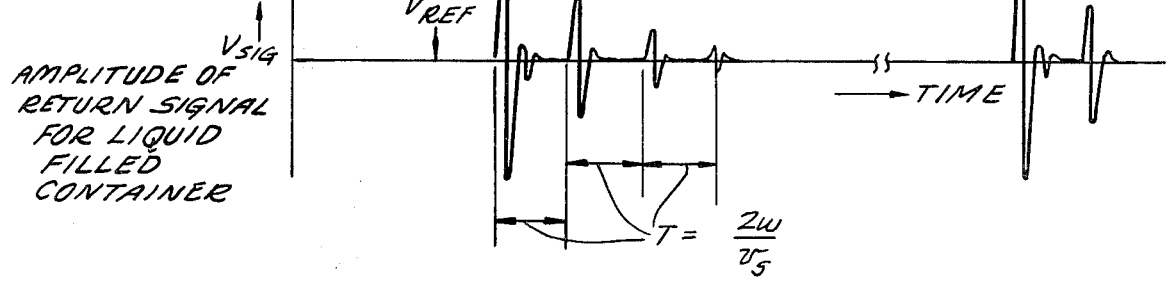
Figure 2C:
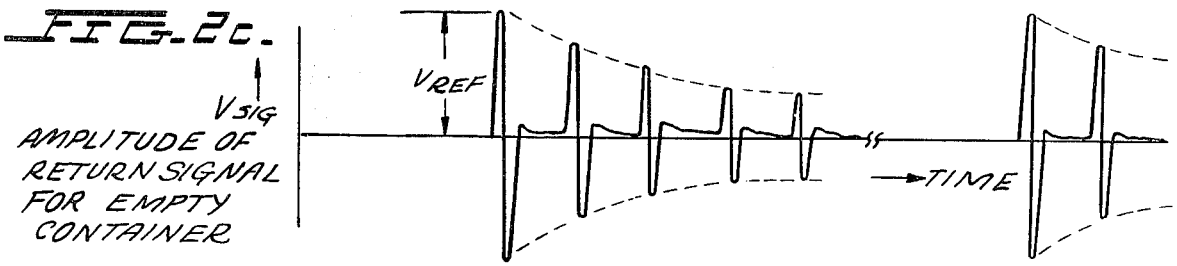

The attenuation of the return signal is illustrated in FIGS. 2a, 2b and 2c which show, on a common time base, the transducer transmit pulse (FIG. 2a), and the multiple reflected signal from surface 13 for the situations where the container is full and empty respectively, at the measurement location (FIGS. 2b and 2c respectively). As shown in FIGS. 2b and 2c, the rate of attenuation of the multiple reflections in a full container (at the measurement location) is much greater than for an empty container.

Figure 4:
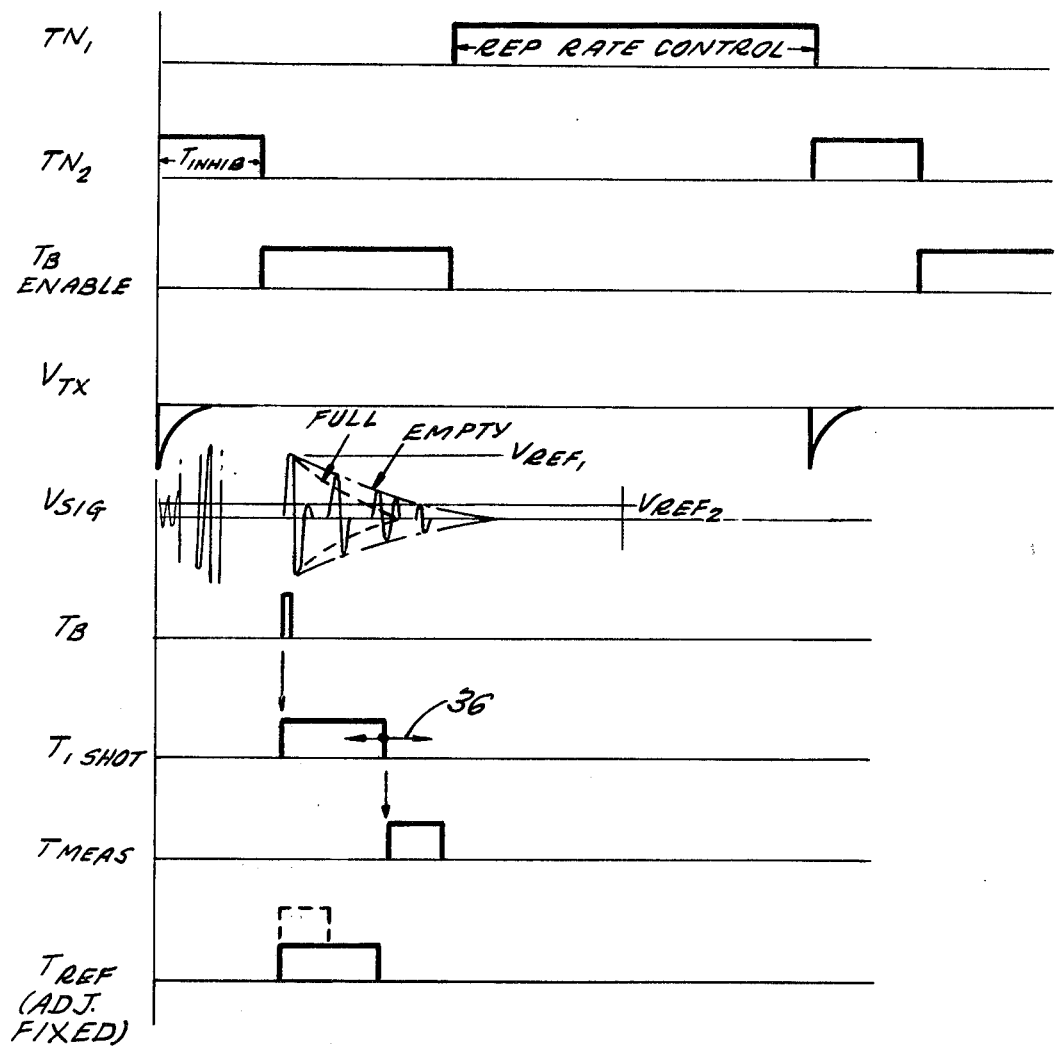
FIG. 4 shows timing diagrams for the circuit of FIG. 3.

FIG. 3 is a functional block diagram of one embodiment of a control unit made in accordance with the present invention, and FIG. 4 is a timing diagram which explains the operation of the unit of FIG. 3.

Referring to FIG. 3, there is illustrated an oscillator 20 connected to transmitter 21, which in turn is connected to multiplexer circuit 22. Multiplexer 22 is connected to transducer 10 and to an amplifier 23.

An inhibiting circuit 24 is provided for inhibiting the operation of the circuit for a given time $T_{INHB}$ after a voltage transmit pulse $V_{TX}$ (see $V_{TX}$ in the timing diagram of FIG. 4), is applied by transmitter 21 to transducer 10 through multiplexer 22. This allows the noise which follows the transmit pulse to subside before the measurement operation proceeds. The inhibit time $T_{INHB}$ is shown in timing diagram $T_{N_2}$ in FIG. 4.

Inhibiting circuit 24 operates a $T_B$ENABLE circuit 25 in FIG. 3 which enables circuit 25 to produce an output pulse so long as the magnitude of any peak of the reflected signal $V_{SIG}$ received by transducer 10 exceeds some reference voltage level $V_{REF_1}$ as will be later described. The $T_B$ENABLE period is shown in the timing diagram of FIG. 4. A repetition rate control circuit 30 is connected to transmit oscillator 20 and allows a transmit pulse $V_{TX}$ to be produced at the end of the $T_{N_1}$ interval shown on the $T_{N_1}$ line in FIG. 4.

The return signal $V_{SIG}$ shown in the timing diagram will include considerable initial noise following the transmit pulse $V_{TX}$. However, at the end of the time $T_{INHB}$, this noise has subsided, and the signal $V_{SIG}$ is applied to the $T_B$ENABLE system.

The $T_B$ENABLE system produces a pulse as shown in the $T_B$ line of FIG. 4 when any peak in $V_{SIG}$, following the start of $T_B$ENABLE time exceeds a first reference voltage $V_{REF_1}$. This reference voltage is shown in the $V_{SIG}$ timing line. Note that the $V_{SIG}$ return shown has a relatively slow decay rate, and is shown for the case of an empty container at the measurement location. The signal would decay at the rate shown in dotted lines for $V_{SIG}$ if the container is full at the point of measurement.

If the first return signal following $T_B$ENABLE exceeds $V_{REF_1}$, a pulse $T_B$ is produced and is applied through a Δ ALC COMMAND circuit to the automatic level control circuit 31. Circuit 31 reduces the gain of amplifier 23 if there is a $T_B$ pulse and this process continues until the first peak return voltage of $V_{SIG}$ has been reduced, by the change in gain of amplifier 23, to the voltage $V_{REF_1}$. The Δ ALC COMMAND circuit identifies whether the gain of amplifier 23 is to be increased or decreased. This process insures that the measuring circuit is identically calibrated for all measurements even though external conditions might change such as varying coupling between the transducer 10 and the container 11, and the like.

The timing diagram for $V_{SIG}$ shows a second reference voltage $V_{REF_2}$ which is lower than $V_{REF_1}$, by a given amount and for example, may be twenty percent of $V_{REF_1}$. The voltage $V_{REF_2}$ is applied to reference comparison circuit 32 which compares the value of the voltage of any peak $V_{SIG}$ to $V_{REF_2}$ and produces an output to comparison gate 33 so long as the peak return in $V_{SIG}$ exceeds $V_{REF_2}$. Thus, if the container is empty, the signal from gate 33 will be much longer than when the pipe is full and $V_{SIG}$ is more sharply damped.

The circuit for determining the length of time taken for $V_{SIG}$ to decay from $V_{REF_1}$ to $V_{REF_2}$ includes one-shot 34 which receives $T_B$ as an input. The length of the pulse of one-shot 34 is controlled by Δ T delay control circuit 35. Thus, the trailing edge of the pulse of the one-shot 34 is advanced or retarded, as shown by the arrow 36 in the T one-shot diagram in FIG. 4, and changes the time at which one-shot 38 ($T_{MEAS}$) is fired.

The pulse produced by one-shot 38 and a signal produced each time that $V_{SIG}$ exceeds reference voltage $V_{REF_2}$ are applied to comparison gate 33, and, if the reference voltage is exceeded during the $T_{MEAS}$ pulse, the one-shot 34 pulse is lengthened by control circuit 35. Conversely, the one-shot 34 pulse length is shortened if $T_{MEAS}$ begins after $V_{SIG}$ falls below $V_{REF_2}$. Thus, the length of the pulse from one-shot 34 is a measure of the time taken for the multiple interwall reflection in container 11 to decay from a first peak return having a peak $V_{REF_1}$ to the second voltage reference $V_{REF_2}$.

The pulse length from one-shot 34 is then applied to a pulse width comparison circuit 40 which has a second input from a decay reference circuit 41 while produces a control pulse which has a length adjusted to correspond either to an empty location on the container or a filled location on the container. Thus, before the instrument is used, it is calibrated by applying the transducer to a location on the container which, for example, is known to be full. The decay reference circuit 41 is then adjusted to produce a pulse length which will cause a full indication lamp to be turned on. Thereafter, if the transducer is located at a container-filled location, this length for the pulse from one-shot 34 will correspond to a "full" measure and the full indication circuit 45 will be excited to energize the full indicator lamp 46. If, however, the container is empty at the transducer location, the signal $V_{SIG}$ will take a much longer time to decay from $V_{REF_1}$ to $V_{REF_2}$ so that the pulse width comparison circuit 40 will produce a suitable signal to the empty indication circuit 43 in order to light the empty lamp 44.

It will be apparent that the outputs from circuits 43 and 45 could be applied to any desired control circuit or the like. It is also possible to produce a fault alarm through the relay 50 which is operated by a fault alarm monitoring circuit 51 which receives an output from the pulse width comparison circuit 40. More specifically, the fault alarm circuit 51 can be energized in response to one of two situations. Thus, if the transducer 10 is not properly coupled to the container 11, there will be no $T_B$ pulse produced since no peak of the $V_{SIG}$ return will be larger than the $V_{REF_1}$. Consequently, there will be no output from one-shot 34 and this information can be used to excite the fault alarm circuit 51.

The second situation which can energize the fault alarm circuit 51 would be the production of a $T_B$ pulse outside the measurement interval. That is, the $T_B$ pulse, as seen in FIG. 4, initiates the measuring interval. If another $T_B$ pulse appears during the measurement, this would be produced due to noise in the circuit and would turn on the fault alarm circuit 51 and fault indicator devices through the operation of the relay 50.

If desired, and as shown in FIG. 3, an anti-slosh relay 60 can be provided in the circuit to provide a settable time delay which, typically, may be from 50 milliseconds to 15 seconds before the relay is closed to enable the operation of the circuit. This feature is useful to prevent the chattering of relay 50 and other relays in the system, and the blinking of lamps such as lamps 44 and 46 due to sloshing of liquid in the tank or pipe under measurement.

The foregoing described the analysis of the return signal to determine whether interface 13 was wall material-to-liquid or wall material-to-air. If desired, the circuit could be calibrated to identify a specific liquid in the container on the basis of its damping effect on a multiply-reflected wave in the container wall, as compared to the damping effect caused by a known liquid. Thus, the damping effect is a function of the sonic impedance in the liquid. The decay time produced by a known liquid may be used to set a reference decay time, which is then compared to the decay time produced by an unknown liquid in the tank. The decay time so measured will then be greater or less than the reference decay time by some given amount, thereby producing a measure of the sonic impedance in the liquid, thus identifying the liquid.

Figure 6:
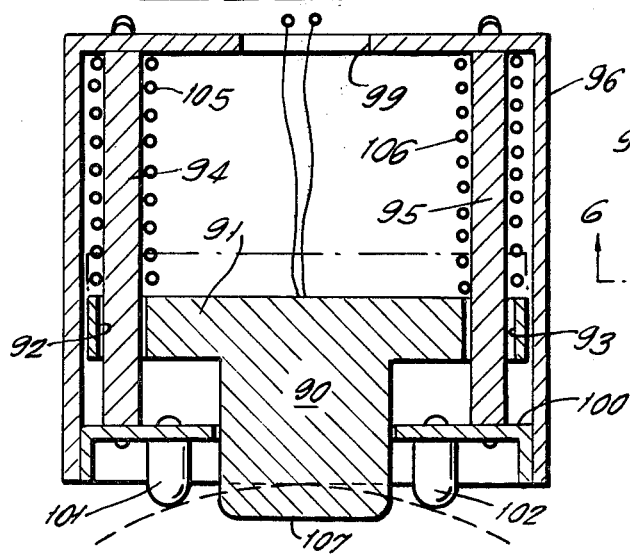
FIG. 6 is a cross-sectional view of FIG. 5 taken across section line 6—6 in FIG. 5.
Figure 5:
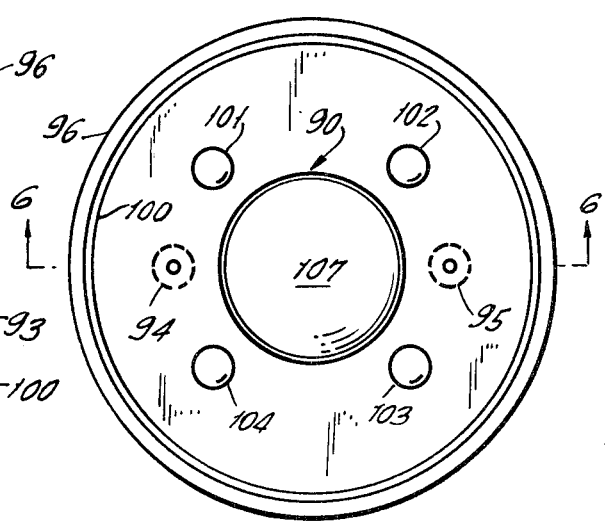
FIG. 5 shows a bottom view of a spring-loaded transducer head made in accordance with the invention.

FIGS. 5 and 6 show a novel transducer structure which can be used by personnel without training, and which insures that the transducer is pressed against a container wall with appropriate pressure. Thus, in FIGS. 5 and 6, the transducer is schematically illustrated as having a transducer crystal assembly 90 which may be of the type shown in FIG. 1, where, however, there is provided a mounting flange 91 (FIG. 6). Flange 91 has guide openings 92 and 93 which receive guide rods 94 and 95, respectively, which are fixed within cylindrical housing 96. The transducer leads 97 and 98 are taken out through a suitable opening 99 in housing 96.

Housing 96 has a base member 100 which has four projecting legs 101 to 104 which project beyond the bottom of housing 96. A pair of biasing springs 105 and 106, surrounding rods 94 and 95, then press the transducer assembly downward toward base 100 with a given pressure.

In operation, the user of the equipment simply presses the end surface 107 of the transducer 90 against the outer wall of a pipe, as schematically shown by dotted lines in FIG. 6, until legs 101 to 104 engage the surface of the pipe. Springs 94 and 95 are then compressed by a given amount to provide the desired pressure between transducer 90 and the container wall.

Although a preferred embodiment of this invention has been described, many variations and modifications will now be apparent to those skilled in the art, and it is preferred therefore that the instant invention be limited not by the specific disclosure herein but only by the appended claims.

I claim:

1. A monitor for a fluid receiving container for determining a fluid condition within the container without penetrating the container wall; said monitor comprising a transducer means operable to be pressed against the outer surface of said container at a given location on said container, a transducer operating circuit for producing an ultrasonic pulse from said transducer means which travels longitudinally into the wall of said container at said given location, and a transducer signal processing circuit for processing the output signal produced by said transducer means in response to the reception thereby of a return multiply reflected ultrasonic signal within the wall of said container at said given location; said signal processing circuit including amplitude decay measuring means for measuring the rate of decay of the amplitude of said return signal and output circuit means for producing an output signal in response to the measured rate of decay of said return signal.

2. The device of claim 1 which further includes amplifier means for normalizing the amplitude of said return signal; said amplifier means varying the amplitude of said return signal until the first return peak in said return signal reaches a predetermined magnitude.

3. The device of claim 1 wherein said transducer means is a single transducer.

4. The device of claim 3 wherein said single transducer is fixed to said surface of said container.

5. The device of claim 3 wherein said single transducer is pressed against said container surface by hand pressure.

6. The device of claim 1 wherein said signal processing circuit produces a first signal responsive to the rate of decay of said return signal when said container is filled with liquid at said given location and a second signal when said container is empty at said given location.

7. The device of claim 2 wherein said signal processing circuit produces a first signal responsive to the rate of decay of said return signal when said container is filled with liquid at said given location and a second signal when said container is empty at said given location.

8. The device of claim 3 wherein said signal processing circuit produces a first signal responsive to the rate of decay of said return signal when said container is filled with liquid at said given location and a second signal when said container is empty at said given location.

9. The device of claim 1 wherein said signal processing circuit produces a first signal responsive to the rate of decay of said return signal when said container is filled with a first medium at said given location and a second signal responsive to the rate of decay of said return signal when said container is filled with a second medium at said given location; said first and second mediums having different characteristic velocities of sound.

10. The device of claim 9 wherein said first and second mediums are both liquids.

11. The device of claim 9 wherein said first and second mediums are gas and liquid respectively.

12. The device of claim 2 wherein said signal processing circuit produces a first signal responsive to the rate of decay of said return signal when said container is filled with a first medium at said given location and a second signal responsive to the rate of decay of said return signal when said container is filled with a second medium at said given location; said first and second mediums having different characteristic velocities of sound.

13. The device of claim 2 which further includes fault alarm circuit means connected to said amplifier means; said fault alarm circuit means being energized when said return signal is not normalized.

14. The device of claim 1 which further includes anti-slosh relay means connected to said signal-processing circuit for preventing the operation of said output circuit means for a given time following the operation of said transducer operating circuit.

15. A process for determining the contents of a container without penetrating said container; said process comprising the injection of a repetitive longitudinal ultrasonic pulse of energy into the wall of said container at a given location thereon; measuring the amplitude of the return signal reflected from the inner wall of said container and adjusting said return signal to a normalized value, measuring the attenuation of said return signal, comparing the measured attenuation to a premeasured attenuation of the return signal when said container has a known medium therein adjacent said given location, and producing an output in response to the comparison of the measured attenuation to said pre-measured attenuation.

16. A process for determining the nature of the contents of a container without requiring physical access to the interior of the container; said process comprising the injection of a repetitive longitudinal ultrasonic pulse of energy into the wall of said container at a reference location known to have a given internal medium therein; measuring the amplitude of the return signal reflected from the inner wall of said container for each pulse, and measuring the attenuation of said return signal to produce a reference attenuation; and thereafter injecting a longitudinal pulse of energy into the wall of said container at a second location thereon and measuring the attenuation of the amplitude of the return signal reflected from the inner wall of said container at said second location; and comparing the attenuation of said return signal at said reference location and at said second location, and producing an output signal in response to said comparison.

17. The process of claim 16 which further includes the step of normalizing said return signal at said reference and second locations before measuring the attenuation of said return signal at said locations.

18. The process of claim 17 wherein a single transducer is moved from said reference location to said second location to inject said ultrasonic pulses into said container.

19. The process of claim 16 wherein said output signal indicates whether said container is empty or filled with liquid at said second location.

20. A transducer monitor for monitoring the presence or absence of liquid in a container at a particular location thereon; said transducer monitor including a transducer for producing a repetitive longitudinal output pulse of ultrasonic energy, a receiving circuit connected to said transducer for producing a return signal responsive to reflected energy received by said transducer; amplifier circuit means connected to said receiving circuit for amplifying said return signal; a normalizing circuit means connected to said amplifier circuit means and including first reference voltage means to cause said amplifier circuit means to amplify the first pulse in said reflected signal to a given first reference voltage magnitude; attenuation measuring circuit means connected to said amplifier circuit means including a second reference circuit means containing a second reference voltage means; the voltage level of said second voltage reference means being lower than that of said first reference voltage means by a given value; first comparison circuit means producing an output when said return signal amplitude attenuates to the level of said second reference voltage means; attenuation time measuring means for measuring the length of time taken for said return signal to attenuate from said first reference level to said second reference level; a reference attenuation time circuit for producing an attenuation time reference related to the presence of a given medium in said container at the point of measurement; second comparison circuit means connected to said attenuation time measuring means and said reference attenuation time circuit for comparing the measured attenuation time to the reference attenuation time; and output circuit means for producing an output in response to the comparison of times in said second comparison signal.

* * * * *